United States Patent [19]

Miller

[11] 4,344,092

[45] Aug. 10, 1982

[54] MINIATURE VIDEO CAMERA MEANS FOR VIDEO SYSTEM

[75] Inventor: Frederick A. Miller, Santa Barbara, Calif.

[73] Assignee: Circon Corporation, Santa Barbara, Calif.

[21] Appl. No.: 199,380

[22] Filed: Oct. 21, 1980

[51] Int. Cl.$^3$ .......................... H04N 5/26; H04N 5/34
[52] U.S. Cl. .................................... 358/217; 358/229
[58] Field of Search ........................ 358/209, 217, 229

[56] References Cited

U.S. PATENT DOCUMENTS 4,028,730  6/1977  Miller .................................. 358/217

OTHER PUBLICATIONS

Proceedings of the National Aerospace Electronics Conference, Dayton, Ohio, 1971.

Primary Examiner—Robert L. Richardson

Attorney, Agent, or Firm—Daniel J. Meaney, Jr.

[57] ABSTRACT

A miniature video camera means adapted for use in a video system having a video imaging means for producing an electrical video signal, a housing means defining an opening therethrough to permit an optical image from an optical device to be focused on an imaging surface of the video imaging means and circuit means formed into a geometric shape which defines a passageway of a geometrical dimension to permit the optical image to pass therethrough and wherein the circuit means is located in the housing between the housing opening and the imaging surface of the video imaging means and wherein the circuit means includes preamplifying means operatively connected to the video imaging means for receiving and amplifying the electrical video signals with a predetermined gain and driving means operatively connected to the preamplifying means and to an output circuit to drive the output circuit with an amplified electrical video signal is shown.

11 Claims, 14 Drawing Figures

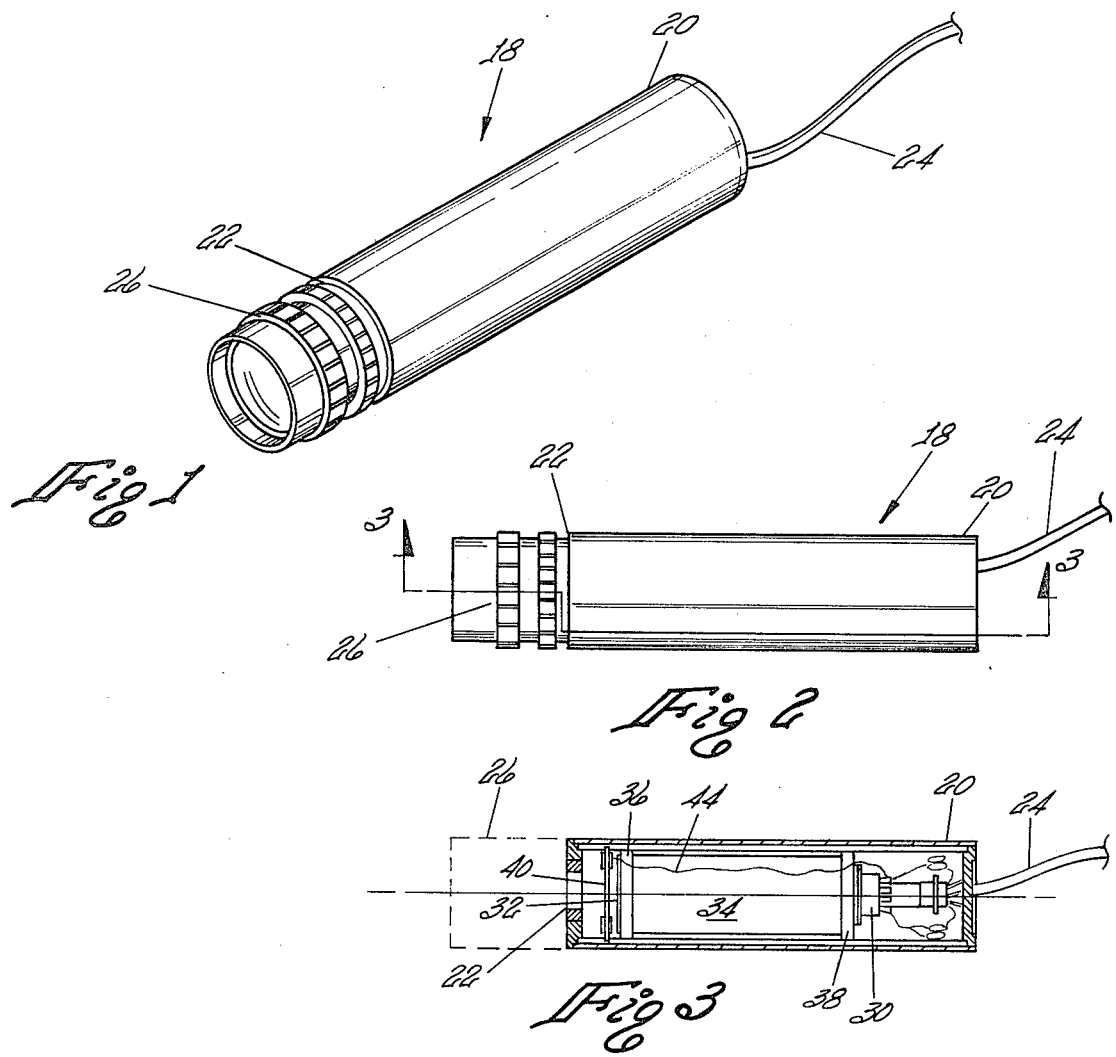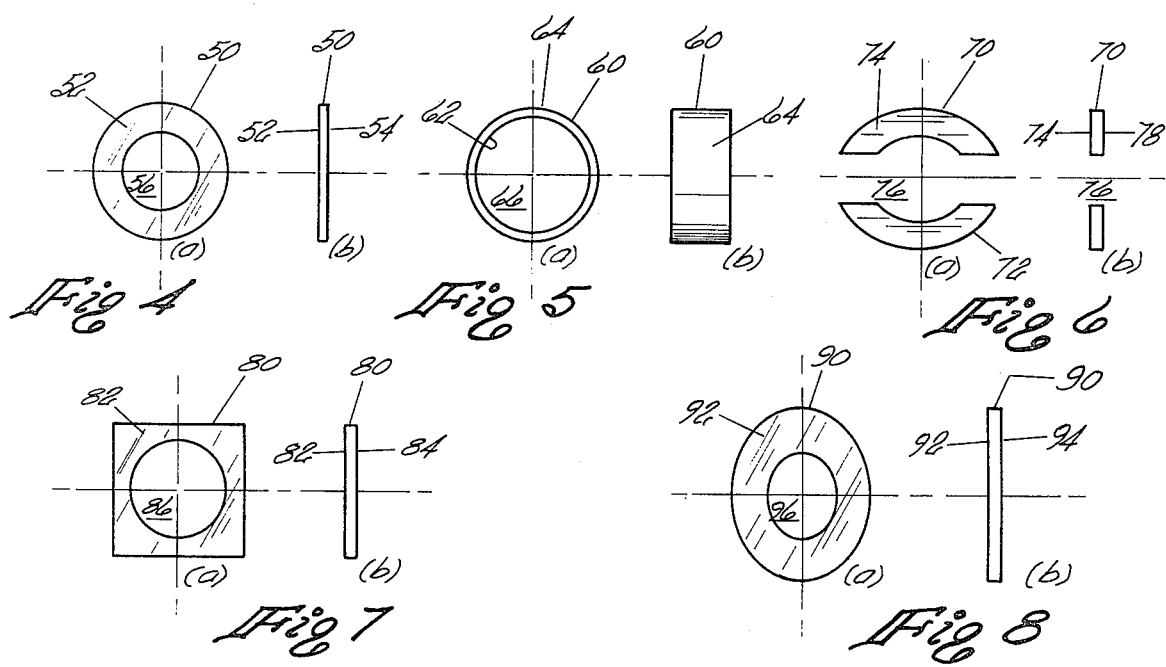

MINIATURE VIDEO CAMERA MEANS FOR VIDEO SYSTEM

BACKGROUND OF THE INVENTION

1. Field of the Invention

This invention relates to a miniature video camera means adapted for use in video systems and more particularly to a small, compact video camera head having a housing which is substantially the same size as a vidicon tube and yoke and which includes circuit means for preamplifying and driving a coaxial cable in a direct wire television system with an amplified video signal.

2. Description of the Prior Art

A video camera head for a closed circuit television system is disclosed in U.S. Pat. No. 4,028,730 to Frederick A. Miller, inventor of the invention described herein and having a common assignee.

The video camera head described in U.S. Pat. No. 4,028,730 is a small compact, lightweight, color video camera and includes a vidicon tube and two printed circuit boards, one of which is positioned between the opening of the metal housing and the vidicon tube and the other of which is located between the rear of the videcon tube and the housing. Due to the electrical components required in order to drive the coaxial cable utilized in a direct wire closed circuit television system with an amplified electrical video signal, a first printed circuit board is utilized for the preamplifying means for producing an amplified, video signal which is then applied to the second printed circuit board located at the opposite end of the housing wherein the electrical video signal is amplified by an amplifying means and applied to an emitter-follower amplifier means to drive a coaxial cable with an amplified electrical video signal.

Recently, use of color video cameras and closed circuit television systems have experienced great expansion in the medical and related fields. As such, it is becoming imperative that the size of the video camera head be reduced so that it can be readily attached to medical optical devices, microscopes and the like. In surgery, components maintained within the sterile field of operation must, of necessity, be reduced to the minimum possible size.

As the size of the known video imaging means is reduced, it becomes more difficult to recover the video signal produced from the video imaging means. It is desirable for the electrical video signals to have a signal to noise ratio of more than forty (40) decibels.

Thus, the length of electrical conductors which extend from printed circuit boards in the video camera head and the capacitive effect thereof results in additional noise into the electrical video signal which reduces the signal to noise ratio of the electrical video signal in the associated television systems.

SUMMARY OF THE INVENTION

The present invention overcomes several disadvantages associated with the miniaturization of color video camera means and video imaging means used therein by minimizing the noise which is introduced into the electrical video signal during the preamplification thereof before the amplified video signal is applied to an output circuit such as for example, a coaxial cable in a closed circuit television system.

The present invention discloses a miniature video camera means for use in a video system. The video camera means includes a video imaging means for producing an electrical video signal and includes an imaging surface for receiving an optical image thereon and for generating an electrical video signal representing the optical image. In the preferred embodiment, an electromagnetic deflection yoke is used. A housing encloses the video imaging means and includes means for defining an opening therethrough at one end thereof enabling an optical image to impinge upon the imaging surface of the video imaging means. The housing encloses and supports the video imaging means with the imaging surface spaced in axial alignment with and a predetermined distance from the opening. Circuit means are provided which can be formed into any desired geometrical shape and which define a passageway which is adapted to pass an optical image. The circuit means is located in the housing between the opening and the imaging surface of the video imaging means and is positioned with the passageway relative to the opening and imaging surface such that the optical image is passed therethrough and impinges upon the imaging surface of the video imaging means. The circuit means includes preamplifying means and driving means for applying an amplified electrical video signal to an output circuit which forms part of a video or television system.

One advantage of the present invention is that very small video imaging means may be utilized which have diameters in the order of about $\frac{1}{2}''$, $\frac{5}{8}''$, and $\frac{2}{3}''$ to about 1.00'', lengths in the order of about 2'' to 3'' and a weight in the order of 1 ounce.

Another advantage of the present invention is that circuit means can be formed of any construction such as thick film, thin film, printed circuit board, integrated circuit elements, wired electrical components and the like.

A yet further advantage of the present invention is that the preamplifying means of the circuit means can be specifically designed, positioned on the circuit means located in the opening or distance between the opening in the housing end and imaging surface and have circuit characteristics which result in performance characteristics of a miniaturized color video camera which are similar to those of larger competitive video camera means.

Yet a further advantage of the present invention is that the miniaturized color video camera means has electrical characteristics which are equivalent to that of larger cameras including sensitivity, resolution and chroma.

A still yet further advantage of the present invention is that the video camera means is electrically connected by a shielded coaxial cable to processor circuitry which is located remote to the video camera means. In the video camera means, low impedance horizontal drive circuits and a low impedance horizontal electromagnetic deflection yoke having an inductance of less than 0.5 millihenries can be utilized with the video imaging means without affecting sensitivity, resolution, or chroma of the video signal generated thereby. Of course, video imaging means having electrostatic deflecting means could likewise to used herein.

BRIEF DESCRIPTION OF THE DRAWING

The foregoing and other advantages of this invention will be apparent from the following description of the preferred embodiment of the invention when considered with the illustrations and the accompanying drawing which includes the following figures:

FIG. 1 is a perspective view of a miniature video camera means utilizing the teaching of this present invention;

FIG. 2 is a top plan view of a video camera means;

FIG. 3 is a partial sectional view of the video camera means taken along section lines 3—3 of FIG. 2;

FIGS. 4 (a) and 4 (b) are pictorial representations of an annular shaped circuit means having an annular shaped passageway;

FIGS. 5 (a) and 5 (b) are pictorial representations of a cylindrical shaped circuit means which includes a hollowed out central area which defines a passageway;

FIGS. 7 (a) and 7 (b) are pictorial representations of rectangular shaped circuit means having an annular shaped passageway;

FIGS. 8 (a) and 8 (b) are pictorial representations of an oval shaped circuit means having an optical shaped means defining a passageway; and FIG. 9 is a schematic diagram of the electrical circuitry of the circuit means including a preamplifying means, driving curcuit means and an output circuit.

DESCRIPTION OF THE PREFERRED EMBODIMENT

Figure 6:
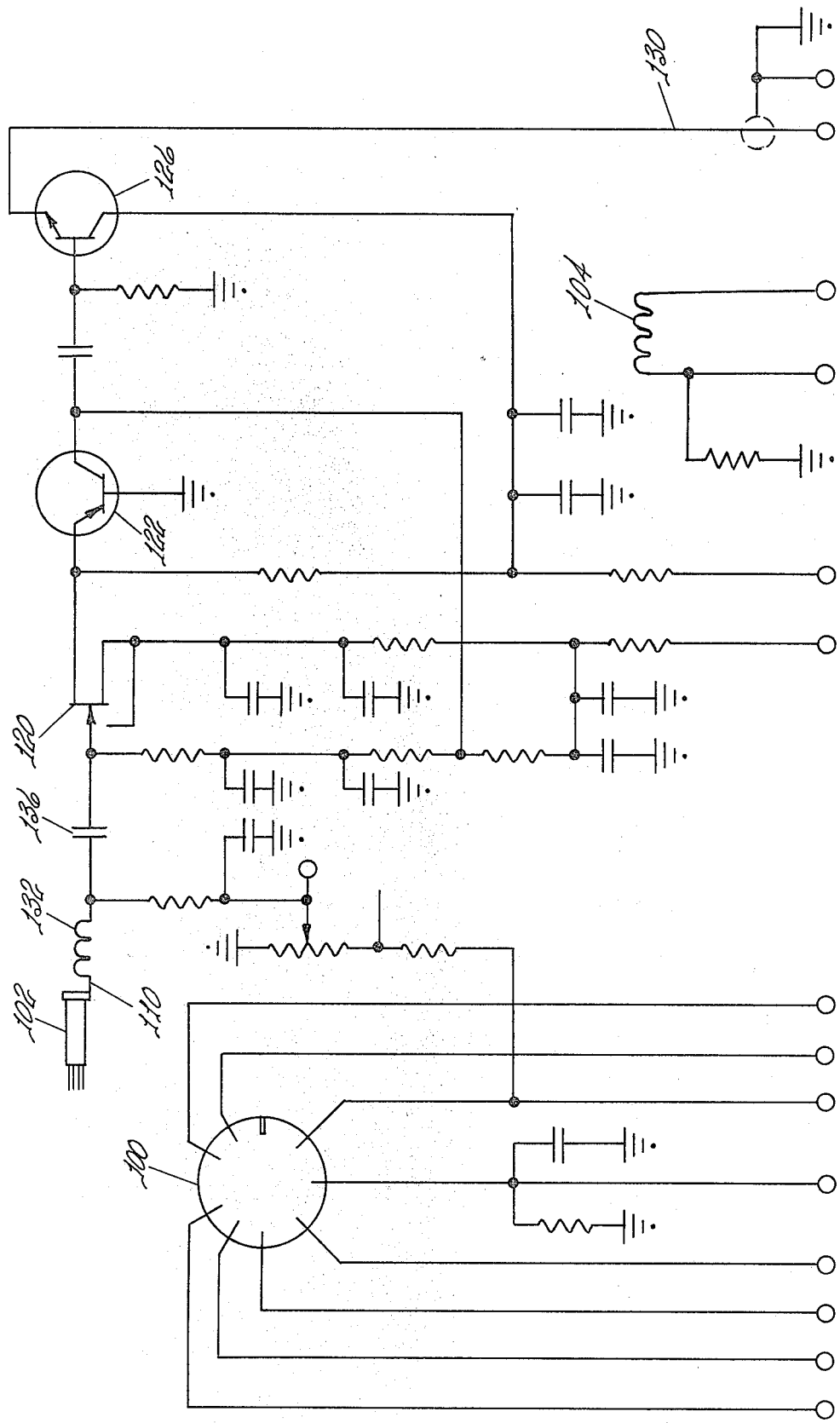
FIGS. 6 (a) and 6 (b) are pictorial representations of a two segment semi-circular circuit means which defines a passageway therebetween.

FIG. 1 illustrates a miniature video camera means shown generally by arrow 18 which is adapted for use in a video system. In the preferred embodiment, the video camera means is adapted for use in a closed circuit, direct wire television system. However, it is envisioned that the video camera means could have wide application including use in any type of a video system, television system, broadcasting system, any type of radio requency transmission system or the like.

The video camera means illustrated in FIG. 1 includes a housing 20 which encloses and supports a video imaging means which is illustrated in greater detail in FIG. 3. The video camera means 18 includes a housing 20 which encloses and supports a video imaging means. The housing 20 includes means for defining an opening, shown generally as 22, which is adapted to pass an optical image from an optical device, such as for example lens 26, which is located exterior to the housing 20, through the housing 20 onto the imaging surface of a video imaging means.

FIG. 2 illustrates the housing 20, the opening 22, an output circuit 24 in the form of a coaxial cable and lens 26. For purposes hereof, the term "output circuit" is utilized to cover any type of output means such as one or more wires, a coaxial cable, video processing circuitry or the like. In the preferred embodiment, the amplified electric video signal produced by the video camera means 18 is supplied by a coaxial cable to video processing circuitry not shown. However, it is envisioned that any type of communication means, such as a microwave transmitter, direct wire, or other similar type of communication could be utilized to transmit the electrical video signal produced by the video camera means 18.

FIG. 3 illustrates the details and construction of the video camera means which includes a video imaging means 30 which includes an imaging surface 32 for receiving an optical image thereon. The video imaging means 30 generates a video signal representing an optical image received from an optical device such as for example from lens 26.

In application, it is envisioned that the optical image could be produced from a variety of optical devices external to the housing 20. For example, in certain medical applications such as surgery, the video camera can be operatively coupled at the end of the housing to a device which produces an optical image of the interior of a human body such as for example an endoscope. Also, it is further envisioned that the video camera means could be operatively connected to an optical device such as a microscope or the like in order to produce an electrical video signal representative of an optical image applied to the imaging surface of the video imaging means 30.

In one embodiment of the present invention, a video imaging means 30 comprised a vidicon tube having electrostatic focus and electromagnetic deflection. One example of such a vidicon tube is that offered for sale by Matsushita Corporation as type S4094 having a $\frac{2}{3}''$ diameter. The length of the vidicon tube, without socket, is approximately 3.0''. The imaging surface utilizes a stripped two color filter in order to recover the color information from the optical image.

In the preferred embodiment, the video imaging means is a color video imaging means and includes means for generating an electrical video signal having the appropriate video imaging means blanking signals formed therein. The composite video signal is produced by a video processing circuit which is located remote to the video camera means. In operation, the video processing circuitry located remote from the video camera means receives the amplified video signal and produces a composite video signal having appropriate blanking, horizontal synchronizing signals, vertical synchronizing signals, color burst signals and any other electrical signals required to produce information contained within a composite video signal.

Referring again to FIG. 3, the housing 20 includes means for defining the opening 22 which is adapted to pass an optical image therethrough and to permit the optical image to impinge upon the imaging surface 32 of the video imaging means 30.

As noted above, in the preferred embodiment, the video imaging means is a vidicon tube 30. In this embodiment, electromagnetic deflection yoke 34 is positioned around the periphery of vidicon tube 30 and functions as an electromagnetic deflection means.

A circuit means, which in the preferred embodiment is a printed circuit board 40 having a plurality of electrical components mounted thereon, is formed into a predetermined geometrical shape which defines a passageway which is adapted to pass an optical image through the opening 22 of the housing 20 onto the imaging surface 32 of the video imaging means 30.

The circuit means can be one or more sections or segments formed into a number of predetermined geometrical shapes and can be fabricated by using any one of several known techniques. FIGS. 4 (a) and 4 (b) pictorially represent a circuit means which is annular shaped and in the form of a printed circuit board 50 which is constructed using known lamination techniques. The electrical components may be installed on sides 52 and 54 of the printed circuit board 50. The predetermined geometrical shape of the circuit means includes an annular shaped opening or aperture 56 which defines a passage-way which is adapted to pass an optical image. The circuit means is located in the housing at the location of the circuit means 40 as illustrated in FIG. 3, between the opening 22 and the imaging surface 32 such that the passageway 56 of the printed circuit board 50 is positioned relative to the opening 22 and the imaging surface 32 to pass the optical image from the opening 22, through the passageway 56 onto the imaging surface 32.

An alternate embodiment of the printed circuit board is illustrated in FIGS. 5 (*a*) and 5 (*b*) wherein the printed circuit board 60 is a cylindrical shaped circuit means which includes an outer surface 64 and an inner surface 62 and includes a hollowed out central area which defines a passageway 66. Electrical components can be mounted on the cylindrical shaped printed circuit board 60 on either the exterior surface 64 or the inner surface 62, with care being taken that the geometrical dimension of the electrical components on the inner surface 62 does not interfere with the optical image passing through the passageway 66.

FIGS. 6 (*a*) and 6 (*b*) illustrates that the circuit means can be a double segmented or two segmented semi-circular device having an upper segment 70 and a lower segment 72. Electrical components can be mounted on side 74 or side 78. The two segments 70 and 72 are semi-circular in shape and define a passageway 76 which is located therebetween.

Another embodiment for the printed circuit board is illustrated in FIG. 7. The printed circuit board 80 can be rectangular in shape having a geometrical dimension which would enable the same to be inserted into the same position between the video camera means 18 within housing 20 in substantially the same position as circuit means 40 is illustrated in FIG. 3. The printed circuit board 80 of FIG. 7 has a rectangular shaped exterior section and includes an aperture or opening which defines a passageway 86. Components can be mounted on the rectangular shaped printed circuit board 80 on surface 82 or 84.

Another embodiment of the printed circuit board is illustrated by oval shaped printed circuit board 90 which includes printed circuit board.

With the present state of the art, any number of elements may be used for fabricating the circuit means. For example, in the preferred embodiment, the printed circuit board is formed of an insulating base material having copper conductors laminated thereto wherein the copper conductors are fabricated into a predetermined pattern. Electrical components in terms of integrated circuitry, discreet components such as field effect transistors, npn transistors and pnp transistors can be mounted upon the so-formed printed circuit board.

However, with the present state of technology, it is envisioned that the circuit means could be in the form of a single specially designed integrated circuit element such as a large scale integrated circuit, could be fabricated of a plurality of integrated circuit components, could be formed by thin film techniques, thick film substrates, thin film substrates, wired components or any combinations thereof.

One of the important elements associated with positioning of the circuit means intermediate the opening 22 of housing 20 and the imaging surface 32 of the video imaging means 30 is that the electrical video signal must be applied to the circuit means without significant loss of the electrical video signal produced by the video imaging means. Specifically, the so produced electrical signal has a desired signal to noise ratio of about 40 decibels or better and the impedance of the video imaging means is extremely high on the order of about 200 megohms and it is necessary to apply the same to the circuit means with minimal loss to the electrical video signal. Further, the frequency response of the electrical video signal is in excess of 4 MegaHertz and the circuit means must be able to handle this frequency response.

In order to utilize the so produced electrical video signal, it is necessary to preamplify the electrical video signal while maintaining its frequency response and while avoiding the degrading of the signal to noise ratio. The output of the preamplifying means must be of a low impedance, in the order of about 75 ohms, in order to effectively apply the same to an output means.

If the electrical video signal received from the video imaging means is applied directly to leads which conduct the same to printed circuit boards located rearward of the video imaging means without an intermediate preamplifying means, the electrical video signal would be lost.

Further, the length of the electrical conductor between the video imaging means and the circuit means has a capacitance associated therewith. The longer the length of the electrical conductors, the greater is the capacitive effects thereof, such that the high frequency signals are degraded to a lower level where the video signal must be amplified to offset the effects of the electrical conductor capacitance which, in turn, introduces more noise into the electrical video signal.

Therefore, in order to minimize the capacitive effects of leads and other related problems which result in affecting the electrical video signal or which would otherwise degrade the level of the high frequency portion of the electrical video signal, it is essential that the electrical video signal produced by the video imaging means be applied to a high impedance input preamplifying means to immediately and promptly preserve the signal to noise ratio of the electrical video signal before that signal is then transmitted along electrical conductors or applied by some type of a driving circuit means to an output circuit. lead 110 and the so produced electrical video signal is applied to a means responsive to the electrical video signal producing a preamplified electric video signal which has a signal to noise ratio which is not degraded relative to that received from the video imaging means 102. In the preferred embodiment, the means for producing the preamplified video signal is in the form of a high impedance preamplifying means, such as for example a field effect transistor 120 which is operatively coupled to the voltage amplifier means, such as for example, a pnp voltage amplifier transistor 122. The amplified electrical video signal is applied to a driving circuit means 126 which in turn is operatively coupled to an output circuit which is a coaxial cable 130. In the preferred embodiment, the driving circuit means 126 is an emitter-follower amplifying means which may be the form of an npn transistor.

The coaxial cable 130 applies the amplified electrical video signal to video processing circuitry located remote from the device. The impedance of the emitter-follower transistor 126 is appropriately matched to the impedance of the coaxial cable to provide for maximum power transfer to the output circuit.

In the preferred embodiment, the video imaging means is a vidicon tube and is represented by the video imaging means 102. The impedance of the horizontal drive of the vidicon tube is selected to be at a value such that a low impedance horizontal electromagnetic deflection yoke has an inductance of less than 0.5 millihenries. The horizontal coil of the electromagnetic deflection yoke is illustrated by element 104 in FIG. 9. The impedance of the horizontal deflection coil 104 is selected such that the horizontal scanning signals which are produced external from the video camera means, are applied to the video imaging means to develop the desired scan pattern.

The electrical conductors which carry the horizontal scanning signals are one of many conductors in a shielded cable which extends from the video camera means to the video processing circuitry. The other conductors are utilized to carry other signals to the video imaging means and includes a coaxial cable for carrying the amplified video signal from the video imaging means to the video processing circuitry. The low impedance of the horizontal coil enables the video processing circuit to apply the horizontal scanning signals to the horizontal deflection coil 104 over the shielded cable without degrading the video signal produced by the video imaging means.

What is claimed is:

1. A video camera means for use in a video system comprising a video imaging means having an imaging surface for receiving an optical image thereon and for generating a video signal representing a said optical image;

a housing having an optical device coupling end enclosing and supporting said video imaging means and including means defining an opening in said optical device coupling end, said housing enclosing and supporting said video imaging means at distance from said opening which distance is determined by the space between the imaging surface and the optical device coupling end to pass a said optical image from an optical device operatively coupled to the housing, through the opening in the optical device coupling end and distance located between each opening and imaging surface onto the imaging surface;

circuit means operatively coupled to said video imaging means and formed into a predetermined geometrical shape which defines a passageway adapted to pass a said optical image, said circuit means being positioned in said distance located between said opening and said imaging surface with said passageway positioned relative to the opening and said imaging surface to permit a said optical image to pass from said opening through said passageway and said distance located between said opening and imaging surface onto said imaging surface, said circuit means including means responsive to said electrical video signal and for producing a preamplified electrical video signal therefrom having signal to noise ratio which is at least 40 decibels; and driving circuit means electrically connected to said preamplifying means and to an output circuit for applying a said amplified video signal having a signal to noise ratio of at least 40 decibels to said output circuit.

2. The video camera means of claim 1 wherein said video imaging means includes a vidicon tube; and an electromagnetic deflection coil positioned around the periphery of said vidicon tube.

3. The video camera means of claim 1 wherein said preamplifying means includes a high impedance preamplifying means operatively coupled to said video imaging means; and a voltage amplifying means operatively coupled to said high impedance preamplifying means and said driving means for applying said amplified video signal to said driving means.

4. The video camera means of claim 3 wherein said high impedance preamplifying means is a field effect transistor and said impedance matching amplifier is a pnp transistor.

5. The video camera means of claim 3 wherein said driving circuit means is an emitter-follower amplifying means.

6. The video camera means of claim 5 wherein said emitter-follower amplifying means is a npn transistor.

7. The video camera means of claim 1 wherein said housing is a hollowed out cylindrical shaped member.

8. The video camera means of claim 1 wherein said circuit means includes a printed circuit board having an opening in the center thereof to define said passageway.

9. The video camera means of claim 1 wherein said circuit means includes a thin film substrate having said preamplifying means, said driving circuit means and an output circuit mounted thereon.

10. The video camera means of claim 1 wherein said circuit means includes a thick film substrate having said preamplifying means, said driving circuit means and an output circuit mounted thereon.

11. The video camera means of claim 8 wherein said circuit means includes integrated circuitry operatively coupled to said printed circuit means and further including electrical conductors extending directly from the output of the video imaging means to such printed circuit boards and said video imaging means includes a low impedance electromagnetic deflecting means.

* * * * *